United States Patent [19]

Machimura et al.

[11] Patent Number: 5,461,082
[45] Date of Patent: Oct. 24, 1995

[54] DRIED ALUMINUM HYDROXIDE GEL, A METHOD FOR PREPARING THE DRIED GEL, AND AN ANTACID

[75] Inventors: Hitoshi Machimura; Hiroshi Kawaguchi; Akira Ohtsuga, all of Kamiichi, Japan

[73] Assignee: Fuji Chemical Industry Co., Ltd., Japan

[21] Appl. No.: 272,044

[22] Filed: Jul. 8, 1994

[30] Foreign Application Priority Data

Jul. 26, 1993 [JP] Japan .................. 5-203593

[51] Int. Cl.⁶ .................. C07F 5/06; A61K 33/08; A61K 33/10
[52] U.S. Cl. .................. 514/568; 424/686; 424/688; 424/691; 424/692; 556/170; 556/179; 556/182; 514/819
[58] Field of Search .................. 514/819; 424/686, 424/688; 556/170, 179; 556/182; 424/691, 692

[56] References Cited

U.S. PATENT DOCUMENTS 4,822,978  4/1989  Wright et al. .................. 536/121
4,842,734  6/1989  Wright et al. .................. 514/191
5,360,793  11/1994  Brooks .................. 514/23

Primary Examiner—Porfirio Nazario-Gonzales
Attorney, Agent, or Firm—Larson & Taylor

[57] ABSTRACT

The object of the present invention is to prepare a dried aluminum hydroxide gel featuring excellent acid neutrizing capacity, but which is also stable.

A dried aluminum hydroxide gel with a chemical composition represented by the following general formulas:

$$(M_2O)_x Al_2O_3 (CO_2)_y R_z \cdot mH_2O$$ or $$[(M_2O)_{x1}(CaO)_{x2}(MgO)_{x3}] Al_2O_3 (CO_2)_y R_z \cdot mH_2O$$

(wherein M is a monovalent alkali metal and R is an organic acid with a valence of two or more. As a result of its organic acid content, the gel is stable and can have a grater aluminum content, thus improving the acid neutrizing capacity of the gel.

3 Claims, No Drawings

DRIED ALUMINUM HYDROXIDE GEL, A METHOD FOR PREPARING THE DRIED GEL, AND AN ANTACID

BACKGROUND OF THE INVENTION

1. Field of the Invention

The present invention relates to a dried aluminum hydroxide gel and a method for preparing it. Furthermore, the present invention relates to an antacid with the dried aluminum hydroxide gel as an active ingredient, which features excellent acid reactivity and acid neutralizing capacity, remains highly stable with respect to both of these properties as it ages, yet features good workability and storability.

2. Prior Art

Dried aluminum hydroxide gel comes in amorphous powder form and has been widely used as an antacid which is an agent that counteracts or neutralizes acidity. However, commercially available dried aluminum hydroxide gels are slow in reacting with gastric acid and are inferior in terms of their immediate effect. In addition, since such dried gels crystallize rapidly and age poorly during the reaction through the drying processes of their manufacture, as well as after their manufacture, they tend to have problems with decreasing acid neutralizing capacity.

In order to solve this problem, a method has been developed in which an aluminum gel is used as an antacid in a slurry state without undergoing drying process. There is another method that has been used in an attempt to improve the conventional method of binding carbonate ions in the gel. This method, in which the alkali ion of the aluminum hydroxide gel is replaced with a divalent ion, such as Ca, to specifically bind the divalent carbonate ion thereto, thereby suppressing hydrolysis, is described in Japanese Examined Patent Publication (Tokukouhei) No. 1-24731.

DETAILED DESCRIPTION OF THE PREFERRED EMBODIMENTS

First Embodiment

With past methods in which the aluminum hydroxide gel is used in a slurry state, it was impossible to use the gel at low temperatures, as it would freeze. At normal to high temperatures, the gel also had problems with rot due to the proliferation of fungi. Therefore, such a method is not desirable in terms of storability and workability. In addition, the latter method of specifically binding the divalent carbonate ion featured a drawback: despite the binding, the aging process of the aluminum hydroxide continues, decreasing its acid neutralizing capacity. The conventional method of binding the carbonate ion featured a significant problem as well. With this method, the stability of the aluminum hydroxide increases as the number of bound carbonate ions increases. However, the $Al_2O_3$ content decreases to the same extent, significantly decreasing the add neutralizing capacity of the aluminum hydroxide.

The present invention has been completed under these circumstances. The object of the present invention is to provide an aluminum hydroxide of a new composition that features excellent add reactivity and acid neutralizing capacity, remains stable as it ages with respect to both of the above-mentioned properties, yet features good storability and workability. The other objects of the present invention are to develop method for preparing this new aluminum hydroxide gel and to create an antacid containing the dried aluminum hydroxide gel.

As a result of an investigation into the achievement of the above-mentioned objects, the present inventors have discovered that a composition of dried aluminum hydroxide gel containing an organic add with a valence of two or more makes the gel stable in terms of both its reactivity with add and its acid neutralizing capacity, and that such gel is easily manufactured. The present inventions's aluminum hydroxide gel has a chemical composition represented by the following general formula:

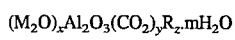

$$(M_2O)_x Al_2O_3 (CO_2)_y R_z \cdot mH_2O$$

wherein M is a monovalent alkali metal; R is an organic acid with a valence of two or more; x, y, z, and m satisfy the expressions $0<x<0.2$, $0.01 \leq y<1$, $0.01 \leq z<1$, and $2 \leq m<10$, respective y and z satisfy the expression $0.1 \leq y+z<1$.

The present invention's aluminum hydroxide gel may also be represented by the following general formula:

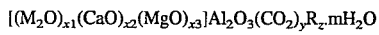

$$[(M_2O)_{x1}(CaO)_{x2}(MgO)_{x3}]Al_2O_3(CO_2)_y R_z \cdot mH_2O$$

wherein M is a monovalent alkali metal; R is an organic acid with a valence of two or more; x1, x2, and x3 satisfy the expressions $0<x1<0.2$, $0<x2<1$, and $0<x3<1$, respectively expression $0.01 \leq y<1$; z satisfies the expression $0.01 \leq z<1$; m satisfies the expression $2 \leq m<10$; x1, x2, and x3 satisfy the expression $0<x1+x2+x3<1$; and y and z satisfy the expression $0.1 \leq y+z<1$.

The dried aluminum hydroxide gel represented by either of the above general formulas features good reactivity with acid. An antacid containing the dried aluminum hydroxide gel as an active ingredient can be an antacid of the present invention. Furthermore, since the dried aluminum hydroxide gel of the present invention is highly reactive with acid, it can be effectively utilized as a cation exchanger and an acid adsorbent, among other things.

The monovalent alkali metal M in the above general formulas is sodium, potassium, or a similar mineral. The present invention is composed of an oxide of the above monovalent alkali metal, $Al_2O_3$ carbonate ions, and an organic acid with a valence of two or more. Specifically, it is the aluminum hydroxide gel of the present invention that contains an organic acid with a valence of two or more. This organic acid and the carbonate ion suppress the hydrolysis of aluminum hydroxide gel, thereby inhibiting its aging. The carbonate ions in the composition of this invention feature a small dissociation constant, and those that bind to the aluminum during the synthesis of a gel are generally monovalent carbonate ions featuring poor binding strength. Accordingly, during the manufacturing process of the gel, from reaction to drying, as well as after manufacturing, the carbonate ions are hydrolyzed and eliminated as bicarbonate ions. As a result, the gel becomes an acid-insoluble, crystalline aluminum hydroxide such as gibbsite. With respect to the attempt to replace the monovalent alkali metal with calcium, magnesium or a similar mineral, thereby specifically binding the divalent carbonate ions, the acid neutralizing capacity of aluminum hydroxide gel treated in this manner deteriorates significantly with age, as will be shown in later examples. Therefore, carbonate ions alone cannot provide the aluminum hydroxide gel with sufficient stability and antacid activity.

The dried aluminum hydroxide gel of the present invention contains an organic acid with a valence of two or more. This organic acid has a greater dissociation constant than does the carbonate ion. The organic acid also binds more strongly to aluminum during gel synthesis. Accordingly, the gel's hydrolysis is suppressed and its stability is improved.

It is preferable that the sum of the carbonate ion and the organic acid, y+z, satisfies the expression $0.1 \leq y+z <1$. When the value of y+z is less than 0.1, the gel becomes unstable. On the other hand, when the value of y+z is greater than 1, the $Al_2O_3$ content decreases relatively and gels add neutralizing capacity per constant weight also decreases, making the gel useless in practice.

Additionally, in the present invention it is also possible to replace the above alkali metal, which has recently become a problem as a result of its hypertension-inducing qualities, with Ca and/or Mg ions, thereby obtaining a highly safe, dried aluminum hydroxide gel.

The antacid of the present invention contains the above dried aluminum hydroxide gel. With respect to the form this antacid may take, nearly any form can be selected: dispersions, granules, fine granules, tablets, suspensions, and syrups. If necessary, diluents, excipients, and disintegrating agents may be added. According to the Japanese Pharmacopoeia, the maximum dose of an antacid should be 3 g/day, but the dose may be varied depending on the patient's condition. The use of such an antacid rapidly neutralizes gastric acid up to approximately pH3, and the acid neutralizing capacity of the antacid expressed as the amount of 0.1N HCl consumed is 300 ml/g or more. In addition, as demonstrated in later examples, the dried aluminum hydroxide gel of the present invention showed a value of 250 ml or more, even after a severe aging test. This value is sufficient for an effective antacid.

The dried aluminum hydroxide gel of the present invention can be prepared by reacting a soluble aluminum compound, a carbonate-ion-supplying compound, and an organic add with a valence of two or more and/or a salt thereof, at a pH level of between 5 and 10. Furthermore, in the present invention, the alkali metal of the resultant gel can be replaced with calcium and/or magnesium through ion exchange.

The soluble aluminum compound used in the above reaction include aluminum chloride, aluminum nitrate, aluminum sulfate, aluminum metal, sodium aluminum sulfate, ammonium aluminum sulfate, aliminum bromide, aluminum fluoride, potassium aluminum sulfate, aluminum isopropoxide, sodium aluminate, and potassium aluminate: one or more of these compounds may be selected.

With respect to the carbonate-ion-supplying compound, one or more of the following may be used: sodium carbonate, potassium carbonate, sodium bicarbonate, potassium bicarbonate, urea, and carbon dioxide.

With respect to the organic acid, divalent aliphatic saturated dicarboxylic adds such as tartaric acid, oxalic acid, malonic acid, succinic acid, glutaric acid, adipic acid, pimelic add, suberic acid, azelaic add, and sebacic acid; divalent aliphatic unsaturated carboxylic acids such as maleic acid, fumaric acid, citraconic acid, and mesaconic acid; and divalent aromatic carboxylic adds such as phthalic acid, isophthalic acid, and terephthalic acid may be used independently or in a mixture. In addition, citric acid can be used as a trivalent organic acid alone or in combination with a divalent organic acid. Furthermore, in the present invention, salts of these organic acids may also be used.

Reaction of the soluble aluminum compound, carbonate-ion-supplying compound, and organic acid and/or salt thereof can be performed in water or a low-alcohol medium at a pH level of 5 to 10. To adjust the pH level during these reactions, alkaline substances such as ammonium, ammonium hydroxide, sodium hydroxide, and potassium hydroxide may be used. The aluminum hydroxide gel produced through the reaction is washed with water and then air-dried by a warm wind or vacuum dried, etc. Thus, the dried aluminum hydroxide gel represented by the previously mentioned general formula $(M_2O)_xAl_2O_3(CO_2)_yR_z \cdot mH_2O$ can be obtained.

In another embodiment of the present invention, the aluminum hydroxide gel produced through the above reaction may be subjected to ion exchange to replace the monovalent alkali metal therein with calcium and/or magnesium. The ion exchange can be conducted by contacting the aluminum hydroxide gel with calcium and/or magnesium. For example, the gel can be poured into or washed with a solution containing calcium and/or magnesium. One or more of the following calcium-and/or magnesium-containing compounds may be used in this ion exchange: calcium chloride, calcium nitrate, calcium fluorate, magnesium chloride, magnesium nitrate, magnesium sulfate, magnesium fluorate, magnesium iodide, concentrated seawater, and bittern. After the ion exchange has taken place, the gel is washed and dried to obtain the dried aluminum hydroxide gel represented by the following general formula:

$$[(M_2O)_{x1}(CaO)_{x2}(MgO)_{x3}]Al_2O_3(CO_2)_yR_z \cdot mH_2O.$$

Second Embodiment

Example 1

Water was added to 886.5 g of an aluminum sulfate solution containing 7.31 weight % of $Al_2O_3$, to make 1,000 ml of solution, which is designated as Solution A. In addition, water was added to mixture of 192.9 g of 99.5 weight % sodium carbonate, 25.7 g of sodium succinate $(Na_2C_4H_4O_4) \cdot 6H_2O$, and 100 g of 50 weight % sodium hydroxide solution, to make 1,000 ml of solution, which is designated as Solution B..

Two hundred ml of water was then added to a 400 ml reaction vessel equipped with an overflow recovery function. While being sufficiently stirred, Solutions A and B, respectively, were fed into the vessel through measuring pumps at a rate of approximately 40 ml/min and then synthesized under the following conditions:

Molar ratio of the total amount of carbonate ions and organic acid to $Al_2O_3$:

$$(CO_2+R)/Al_2O_3 = 3.00$$

Molar ratio of organic acid to the total amount of organic acid and carbonate ions:

$$R/(CO_2+R) = 0.05$$

Reaction temperature: 25° C.

pH: Reaction was conducted at a pH level of 7. Adjustments were made using a 25% NaOH solution The solution that overflowed from the vessel during the reaction was recovered and dehydrated to form a cake using a Buchner funnel under reduced-pressure conditions. The cake was then washed with a quantity of water equivalent to 200 times of the $Al_2O_3$ content in weight. After it was washed, the cake was dried overnight at approximately 70° C. The resultant dried, white aluminum hydroxide gel was subjected to chemical analysis, and it was determined that it had the following composition:

$$(Na_2O)_{0.1}Al_2O_3(CO_2)_{0.6}R_{1.7} \cdot 2.82H_2O.$$

The X-ray action pattern was then measured on this dried gel powder, and it was found to be amorphous.

Example 2

The reaction solution obtained above in Example I was dehydrated to form a cake using a Buchner funnel under reduced-pressure conditions. Then cake was then ion-exchanged by washing it with a quantity of 0.02 mol/l aqueous calcium chloride solution equivalent to 100 times the $Al_2O_3$ a content in weight. The cake was subsequently washed with a quantity of water equivalent to 100 times the $Al_2O_3$ content in weight, and was then dried at approximately 70° C. for 20 hours. The resultant dried white aluminum hydroxide gel was subjected to chemical analysis, and it was determined that it had the following composition:

$(Na_2O)_{0.01}(CaO)_{0.24}Al_2O_3(CO_2)_{0.62}R_{0.17}\cdot 2.71H_2O.$

The X-ray diffraction pattern was then measured on this dried gel powder, and it was found to be amorphous.

Example 3

Water was added to 306.8 g of aluminum chloride.$6H_2O$ to make 1,000 ml of solution, which was designated Solution C. In addition, water was added to a mixture of 134.7 g of 99.5 weight % sodium carbonate, 3.75 g of sodium citrate.$H_2O$, and 165 g of 50 weight % sodium hydroxide solution to make 1,000 ml of solution, which was designated as Solution D.

Two hundred ml of water was then added to a 400 ml reaction vessel equipped with an overflow recovery function. While being sufficiently stirred, Solutions C and D, respectively, were fed in to the vessel through measuring pumps at a rate of approximately 40 ml/min and then synthesized under the following conditions:

Molar ratio of the total amount of carbonate ions and organic acid to $Al_2O_3$:

$(CO_2+R)/Al_2O_3=2.00$

Molar ratio of organic acid to the total amount of organic acid and carbonate ions:

$R/(CO_2+R) = 0.01$

Reaction temperature: 25° C.

pH: Reaction was conducted at a pH level of 7. Adjustments were made using a 25% NaOH solution.

The solution that overflowed from the vessel during the reaction was recovered and dehydrated to form a cake using a Buchner funnel under reduced-pressure conditions. The cake was then washed with a quantity of water equivalent to 200 times the $Al_2O_3$ content in weight After it was washed, the cake was dried overnight at approximately 70° C. The resultant, dried, white aluminum hydroxide gel was subjected to chemical analysis, and it was determined that it had the following composition:

$(Na_2O)_{0.09}Al_2O_3(CO_2)_{0.52}R_{0.02}\cdot 3.02H_2O.$

The X-ray diffraction pattern was then measured on this dried gel powder, and it was found to be amorphous.

Example 4

The reaction solution obtained above in Example 3 was dehydrated to form a cake using a Buchner funnel under reduced-pressure conditions. The cake was then ion-exchanged by washing it with a quantity of 0.02 mol/l aqueous magnesium chloride solution equivalent to 40 times the $Al_2O_3$ content in weight. The cake was subsequently washed with a quantity of water equivalent to 100 times the $Al_2O_3$ content in weight, and was then dried at approximately 70° C. for 20 hours. The resultant dried, white aluminum hydroxide gel was subjected to chemical analysis, and it was determined that it had the following composition:

$(Na_2O)_{0.01}(MgO)_{0.23}Al_2O_3(CO_2)_{0.56}R_{0.02}\cdot 2.81H_2O.$

The X-ray diffraction pattern was measured on this dried gel powder, and it was found to be amorphous.

Comparative Example 1

Synthesis was carded out in fundamentally the same manner as in Example 1, except that sodium succinate.$6H_2O$ was not used. The dried aluminum hydroxide gel obtained was found to be amorphous as a result of X-ray diffraction analysis of the dried gel powder.

Comparative Example 2

The dried aluminum hydroxide gel obtained above in Comparative Example 1 was ion-exchanged with calcium in fundamentally the same manner as in Example 2. The resultant dried aluminum hydroxide gel was found to be amorphous as a result of X-ray diffraction analysis of the dried gel powder.

Comparative Example 3

Synthesis was carded out in fundamentally the same manner as in Example 3, except that sodium citrate-$2H_2O$ was not used. The resultant dried aluminum hydroxide gel was found to be amorphous as a result of X-ray diffraction of the dried gel powder.

Concerning the reaction products of Examples 1 through 4 and Comparative Examples 1 through 3, reactivity with acid and resistance to aging were evaluated according to the O.T.C. (over-the-counter) antacid test provided by the U.S. FDA. In addition, the acid neutralizing capacity of the reaction products before aging was evaluated according to the antacid ability testing method provided by the Japanese Pharmacopoeia. The results of these tests are shown in Table 1.

(1) Method for Testing Add-reactivity

Fifty mililiters of 0.1N HCl is placed in a 100 ml beaker, which is then placed in a thermostat set at 37° C. When the liquid in the beaker reaches 37° C., it is agitated with a magnetic stirrer at 300 r.p.m The pH meter's electrode is dipped into the liquid. A 0.8 g powder sample is then added to the liquid while a stop watch is used to measure the time required for the liquid to reach a pH level of 3 to 3.5, as well as to measure the pH level after 10 minutes.

(2) Aging Resistance

A sample is placed in a desiccator containing a saturated sodium chloride solution and is then left at 60° C. for seven days. The resistance to aging of the samples is then determined by conducting the acid-reactivity test described above in (1).

(3) Acid Neutralizing Capacity Test

An aliquot of 0.2 g is precisely weighed from each sample and placed in a flask with a stopper, to which exactly 100 ml of 0.1N HCl is added. The flask is sealed tightly and shaken at a temperature of 37° C.± 2° C. for one hour. The contents are then filtered. Exactly fifty mililiters of filtrate is measured, and the excess HCl is titrated with 0.1N NaOH solution with a pH level of up to 3.5 while being sufficiently stirred. From the titer of 0.1N NaOH, the amount of 0.1N HCl consumed by the sample is determined. The amount of 0.1N HCl consumed per g sample is used as acid neutralizing capacity.

TABLE 1

|  |  | Example 1 | Example 2 | Example 3 | Example 4 | Comparative Example 1 | Comparative Example 2 | Comparative Example 3 |
|---|---|---|---|---|---|---|---|---|
| Before | Reactivity with acid |  |  |  |  |  |  |  |
| aging | Time needed to reach a pH level of 3 | 34" | 48" | 58" | 1' 29' | 4' 18" | 1' 4" | 1' 26" |
|  | Time needed to reach a pH level of 3.5 | 35" | 51" | 1' 02" | 1' 34" | 4' 29" | 1' 8" | 1' 32" |
|  | pH level after ten minutes | 4.09 | 4.12 | 4.08 | 4.03 | 3.97 | 4.03 | 3.99 |
|  | Acid neutralizing capacity (0.1 N HCl ml/g) | 313.7 | 320.5 | 305.4 | 317.2 | 336.9 | 315.9 | 313.6 |
| After | Reactivity with acid |  |  |  |  |  |  |  |
| aging | Time needed to reach a pH level of 3 | 1' 4" | 1' 7" | 1' 50" | 1' 28" | Not reached | 4' 26" | Same as the left |
|  | Time needed to reach a pH level of 3.5 | 1' 40" | 1' 34" | 2' 03" | 1' 57" | Not reached | 5' 6" | Same as the left |
|  | pH level after ten minutes | 3.83 | 3.89 | 3.88 | 3.89 | 2.64 | 3.79 | 2.00 |
|  | Acid neutralizing capacity (0.1 N HCl ml/g) | 278.1 | 286.2 | 268.6 | 268.0 | 103.4 | 177.2 | 79.7 |

As previously described, since the dried aluminum hydroxide gel of the present invention contains an organic acid with a large dissociation constant that suppresses the hydrolysis of the gel, a highly stable gel can be obtained. The dried alminium hydroxide gel of the present invention also displays excellent acid neutralizing capacity when used as an antacid. According to the method of the present invention, this dried gel can be easily prepared.

We claim:

1. A dried aluminum hydroxide gel represented by the following general formula:

$$[(M_2O)_{x1}(CaO)_{x2}(MgO)_{x3}]Al_2O_3(CO_2)_yR_z \cdot mH_2O$$

wherein M is a monovalent alkali metal; R is an organic acid with a valence of two or more; x1, x2, and x3 satisfy the expressions 0<x1<0.2, 0<x2<1, and 0<x3<1, respectively; y satisfies the expression 0.01≦y<1; z satisfies the expression 0.01≦z<1; m satisfies the expression 2≦m<10; x1, x2 and x3 satisfy the expression 0<x1+x2+x3<1; and y and z satisfy the expression 0.1≦y+z<1.

2. A method for preparing the dried aluminum hydroxide gel of claim 1, which entails reacting a soluble aluminum compound, a carbonate-ion-supplying compound, and an organic acid with a valence of two or more and/or a salt thereof, at a pH level between 5 and 10. The monovalent alkali metal in the resultant gel is then ion-exchanged with calcium and/or magnesium.

3. An antacid with dried aluminum hydroxide gel as an active ingredient, as represented by the following general formula:

$$[(M_2O)_{x1}(CaO)_{x2}(MgO)_{x3}]Al_2O_3(CO_2)_yR_z \cdot mH_2O$$

wherein M is a monovalent alkali metal; R is an organic acid with a valence of two or more; x1, x2, and x3 satisfy the expressions 0<x1<0.2, 0<x2<1, and 0<x3<1, respectively; y satisfies the expression 0.01≦y<1; z satisfies the expression 0.01≦z<1; m satisfies the expression 2≦m<10; x1, x2 and x3 satisfy the expression 0<x1+x2+x3<1; and y and z satisfy the expression 0.1≦y+z< 1.

* * * * *